(12) United States Patent
Ortiz et al.

(10) Patent No.: US 7,896,894 B2
(45) Date of Patent: Mar. 1, 2011

(54) APPARATUS FOR SINGLE PASS GASTRIC RESTRICTION

(75) Inventors: Mark S. Ortiz, Milford, OH (US); David B. Griffith, Cincinnati, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1051 days.

(21) Appl. No.: 11/197,543

(22) Filed: Aug. 5, 2005

(65) Prior Publication Data
US 2007/0032800 A1   Feb. 8, 2007

(51) Int. Cl.
*A61B 17/08*   (2006.01)
*A61B 17/04*   (2006.01)

(52) U.S. Cl. .......................................... 606/153; 606/148

(58) Field of Classification Search ................... 606/148, 606/157, 216, 228, 139, 153, 215, 144–147, 606/232, 233; 128/869, 780, 876, 899
See application file for complete search history.

(56) References Cited

U.S. PATENT DOCUMENTS

| | | | |
|---|---|---|---|
| 5,080,663 A | 1/1992 | Mills et al. | |
| 5,188,636 A * | 2/1993 | Fedotov | 606/144 |
| 5,376,101 A | 12/1994 | Green et al. | |
| 5,437,681 A | 8/1995 | Meade et al. | |
| 5,462,558 A | 10/1995 | Kolesa et al. | |
| 5,514,159 A | 5/1996 | Matula et al. | |
| 5,540,705 A | 7/1996 | Meade et al. | |
| 5,571,119 A | 11/1996 | Atala | |
| 5,709,693 A | 1/1998 | Taylor | |
| 5,713,910 A | 2/1998 | Gordon et al. | |
| 5,814,071 A | 9/1998 | McDevitt et al. | |
| 6,036,694 A | 3/2000 | Goble et al. | |
| 6,346,111 B1 | 2/2002 | Gordon et al. | |
| 6,443,962 B1 | 9/2002 | Gaber | |
| 6,454,778 B2 | 9/2002 | Kortenbach | |
| 6,494,888 B1 | 12/2002 | Laufer et al. | |
| 6,506,196 B1 | 1/2003 | Laufer | |
| 6,558,400 B2 | 5/2003 | Deem et al. | |
| 6,641,592 B1 * | 11/2003 | Sauer et al. | 606/144 |
| 6,656,194 B1 | 12/2003 | Gonnoe et al. | |
| 6,663,639 B1 | 12/2003 | Laufer et al. | |
| 6,719,763 B2 | 4/2004 | Chung et al. | |
| 6,719,764 B1 | 4/2004 | Gellman et al. | |
| 6,746,460 B2 | 6/2004 | Gannoe et al. | |

(Continued)

FOREIGN PATENT DOCUMENTS

EP     1545336     6/2005

(Continued)

*Primary Examiner* — (Jackie) Tan-Uyen T Ho
*Assistant Examiner* — Christina Lauer
(74) *Attorney, Agent, or Firm* — Welsh Flaxman & Gitler LLC

(57) ABSTRACT

A gastric reduction apparatus that facilitates the creation of a transoral linear passageway through the stomach includes an elongated body including a proximal end and a distal end. The elongated body is generally sinusoidal shaped with at least one tissue engaging surface oriented such that a needle will pass therethrough. The elongated body also includes at least one needle passing channel respectively formed adjacent the at least one tissue engaging surface. The at least one needle passing channel generally passes through the center of the sinusoidal waveforms defined by the at least one tissue engaging surface such that a needle will pass entirely through stomach tissue contacting the tissue engaging surface of the elongated body. The elongated body further includes a suture passing channel.

23 Claims, 6 Drawing Sheets

U.S. PATENT DOCUMENTS

| | | |
|---|---|---|
| 6,755,843 B2 | 6/2004 | Chung et al. |
| 6,773,440 B2 | 8/2004 | Gannoe et al. |
| 6,835,200 B2 | 12/2004 | Laufer et al. |
| 6,908,427 B2 | 6/2005 | Fleener et al. |
| 6,923,819 B2 | 8/2005 | Meade et al. |
| 7,399,304 B2 * | 7/2008 | Gambale et al. ............... 606/139 |
| 2001/0023352 A1 | 9/2001 | Gordon et al. |
| 2002/0107530 A1 | 8/2002 | Sauer et al. |
| 2003/0065359 A1 * | 4/2003 | Weller et al. ................... 606/213 |
| 2003/0083674 A1 | 5/2003 | Gibbens, III |
| 2003/0171760 A1 | 9/2003 | Gambale |
| 2003/0181924 A1 | 9/2003 | Yamamoto et al. |
| 2003/0208209 A1 | 11/2003 | Gambale |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0158125 A1 | 8/2004 | Aznoian |
| 2004/0162568 A1 | 8/2004 | Saadat et al. |
| 2004/0172047 A1 | 9/2004 | Gellman et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |

FOREIGN PATENT DOCUMENTS

| | | |
|---|---|---|
| EP | 1569709 | 9/2005 |
| WO | WO0061012 | 10/2000 |
| WO | WO01/10312 | 2/2001 |
| WO | WO0166001 | 9/2001 |
| WO | WO0189393 | 11/2001 |
| WO | WO02/35980 | 5/2002 |

* cited by examiner

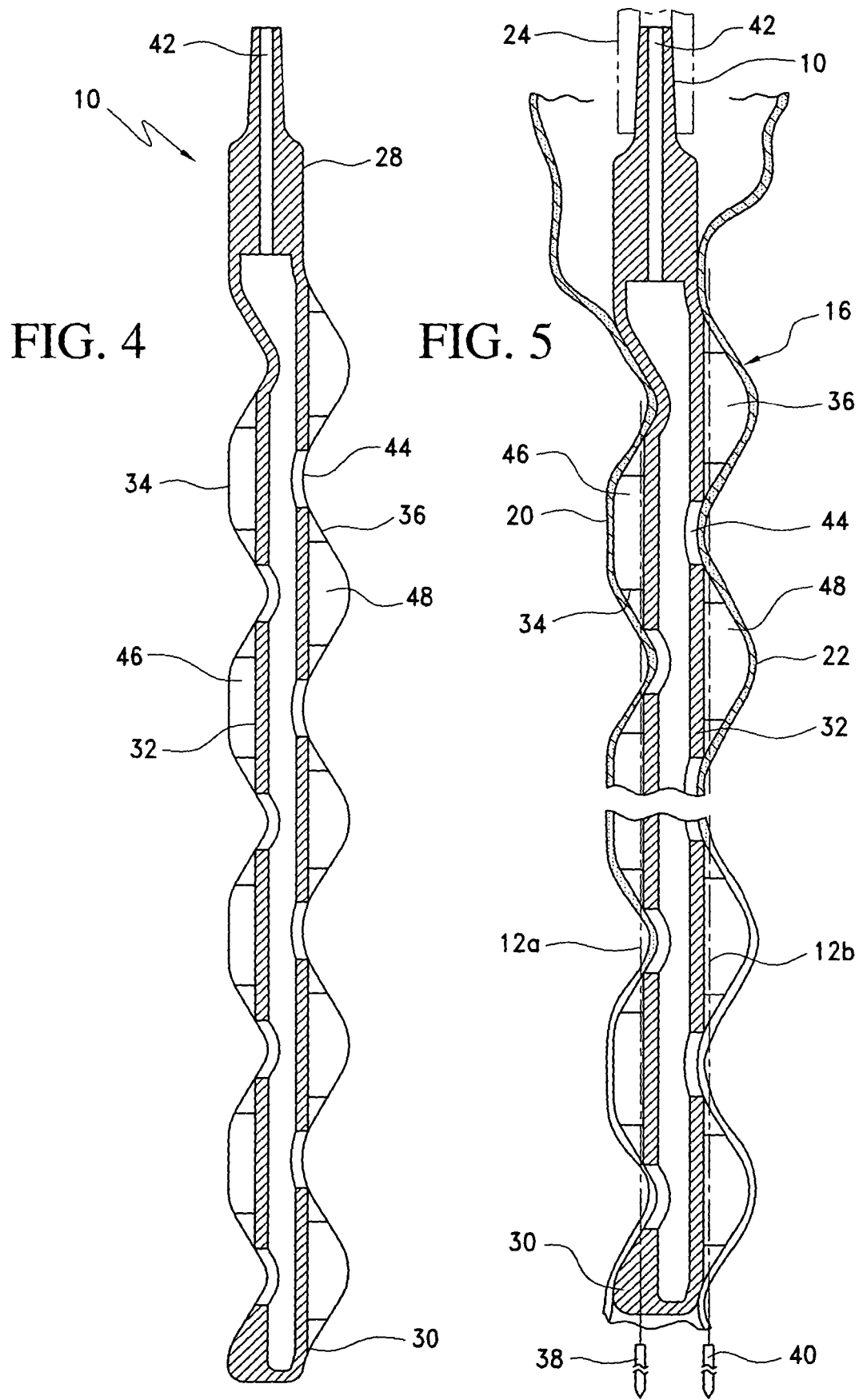

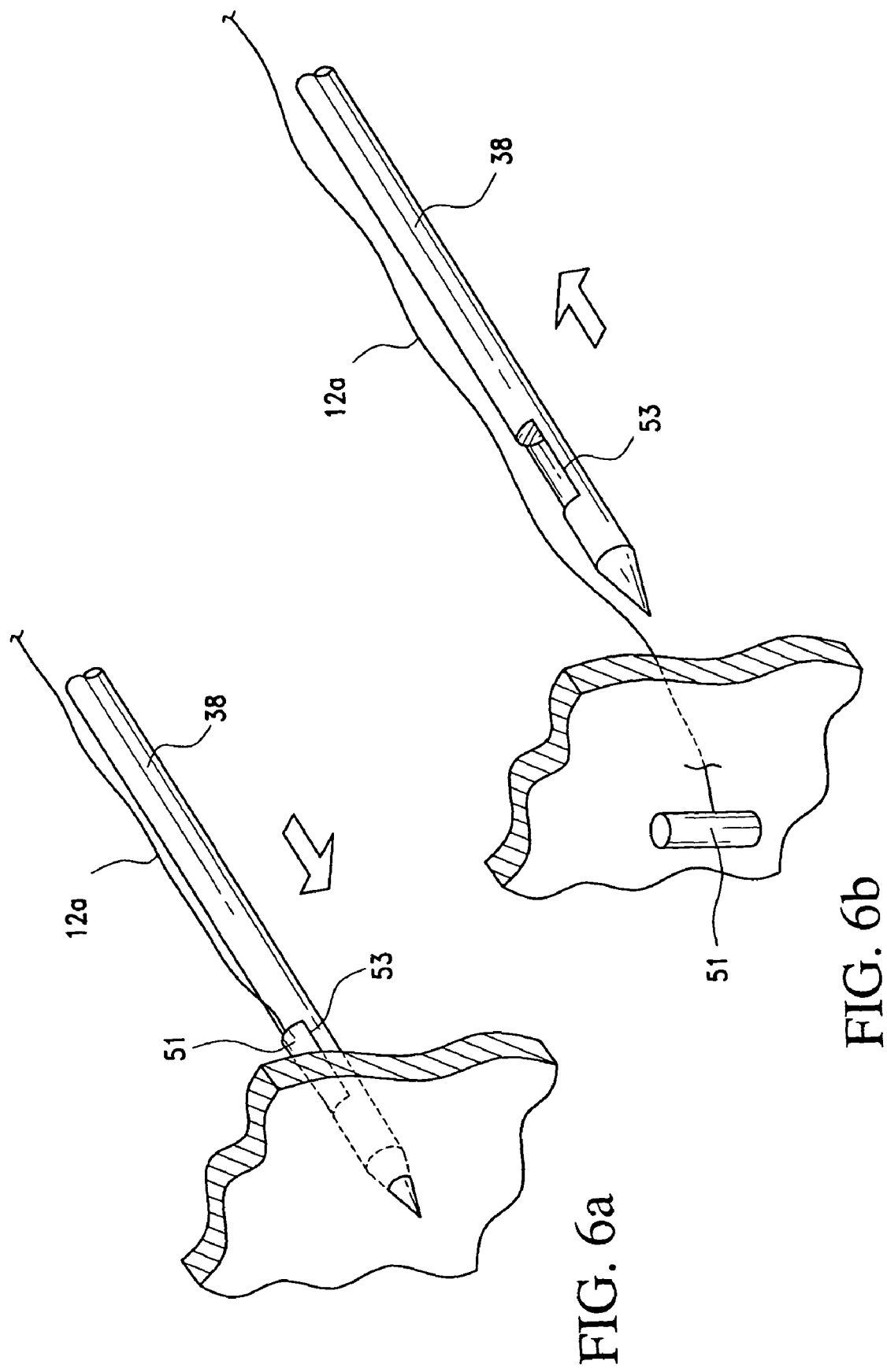

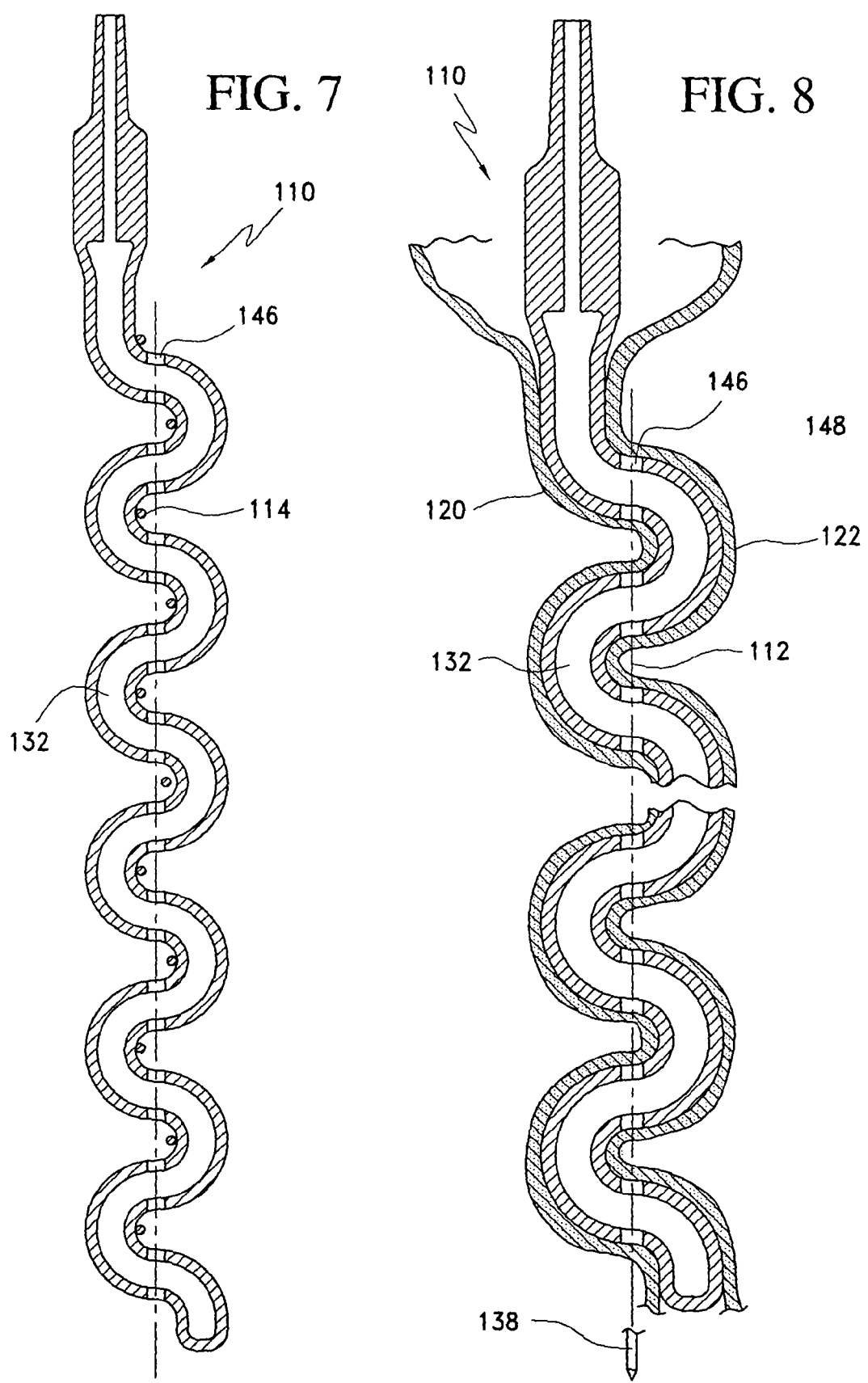

APPARATUS FOR SINGLE PASS GASTRIC RESTRICTION

BACKGROUND OF THE INVENTION

1. Field of the Invention

The present invention relates to gastric reduction surgery. More particularly, the invention relate to a method and apparatus for endoscopically performing gastric reduction surgery.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. The most common currently performed procedure is Roux-en-Y gastric bypass (RYGB). This procedure is highly complex and is commonly utilized to treat people exhibiting morbid obesity. However, with this in mind, greater than 100,000 procedures are performed annually in the United States alone. Other forms of bariatric surgery include Fobi pouch, bilio-pancreatic diversion, and gastroplastic or "stomach stapling". In addition, implantable devices are known which limit the passage of food through the stomach and affect satiety.

RYGB involves movement of the jejunum to a high position using a Roux-en-Y loop. The stomach is completely divided into two unequal portions (a smaller upper portion and a larger lower gastric pouch) using an automatic stapling device. The upper pouch typically measures less than about 1 ounce (or 20 cc), while the larger lower pouch remains generally intact and continues to secrete stomach juices flowing through the intestinal tract.

A segment of the small intestine is then brought from the lower abdomen and joined with the upper pouch to form an anastomosis created through a half-inch opening, also called the stoma. This segment of the small intestine is called the "Roux loop" and carries the food from the upper pouch to the remainder of the intestines, where the food is digested. The remaining lower pouch, and the attached segment of duodenum, are then reconnected to form another anastomotic connection to the Roux loop at a location approximately 50 to 150 cm from the stoma, typically using a stapling instrument. It is at this connection that the digestive juices from the bypass stomach, pancreas, and liver, enter the jejunum and ileum to aid in the digestion of food. Due to the small size of the upper pouch, patients are forced to eat at a slower rate and are satiated much more quickly. This results in a reduction in caloric intake.

The conventional RYGB procedure requires a great deal of operative time. Because of the degree of invasiveness, post-operative recovery time can be quite lengthy and painful.

In view of the highly invasive nature relating to the RYGB procedure, other less invasive procedures have been developed. For example, laparoscopic and other procedures reducing the size of the stomach have been developed. These gastric reduction surgical procedures are conventionally performed to restrict food intake of a patient by decreasing the size of the stomach to a reservoir having a volume on the order of about 15 ml to about 200 ml. The most common form of gastric reduction surgery involves the application of vertical staples along the stomach to create an appropriate pouch. This procedure is commonly performed laparoscopically and as such requires substantial preoperative, operative and postoperative resources. Alternatively, vertical sleeve gastrectomy involves the complete removal of the excluded portion of the stomach.

With the foregoing in mind, procedures that allow for the performance of gastric reduction surgery in a time efficient and patient friendly manner are needed. The present invention provides such a method and an associated apparatus.

SUMMARY OF THE INVENTION

It is, therefore, an object of the present invention to provide a gastric reduction apparatus that facilitates the creation of a transoral passageway through the stomach. The apparatus includes an elongated body including a proximal end and a distal end. The elongated body is generally sinusoidal shaped during deployment with at least one tissue engaging surface oriented such that a needle will pass therethrough. The elongated body also includes at least one needle passing channel respectively formed adjacent the at least one tissue engaging surface. The at least one needle passing channel generally passes through the center of the sinusoidal waveforms defined by the at least one tissue engaging surface such that a needle will pass entirely through stomach tissue contacting the tissue engaging surface of the elongated body. The elongated body further includes a suture passing channel.

It is also an object of the present invention to provide a method for performing gastric reduction surgery. The method is achieved by positioning a gastric reduction apparatus as described above in the stomach, creating a vacuum holding tissue of the stomach wall along the at least one tissue engaging surface of the gastric reduction apparatus, passing at least one needle along the axis of the gastric reduction apparatus through the needle passing channel located adjacent the tissue engaging surface, retracting the needle leaving a purse string suture behind, releasing a pre-woven suture from the gastric reduction apparatus and drawing upon the pre-woven suture causing the pre-woven suture to draw the stomach walls together.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 4 is a cross sectional view of the gastric reduction apparatus.

FIG. 5 is a cross sectional view of the gastric reduction apparatus with tissue drawn into contact with the tissue engaging surfaces.

FIGS. 6a and 6b show the release of an anchor during application of the purse string suture.

FIG. 7 is a cross sectional view of an alternate embodiment of a gastric reduction apparatus in accordance with the present invention.

FIG. 8 is a cross sectional view of the gastric reduction apparatus shown in FIG. 7 with tissue drawn into contact with the tissue engaging surfaces.

DESCRIPTION OF THE PREFERRED EMBODIMENTS

Figure 1:
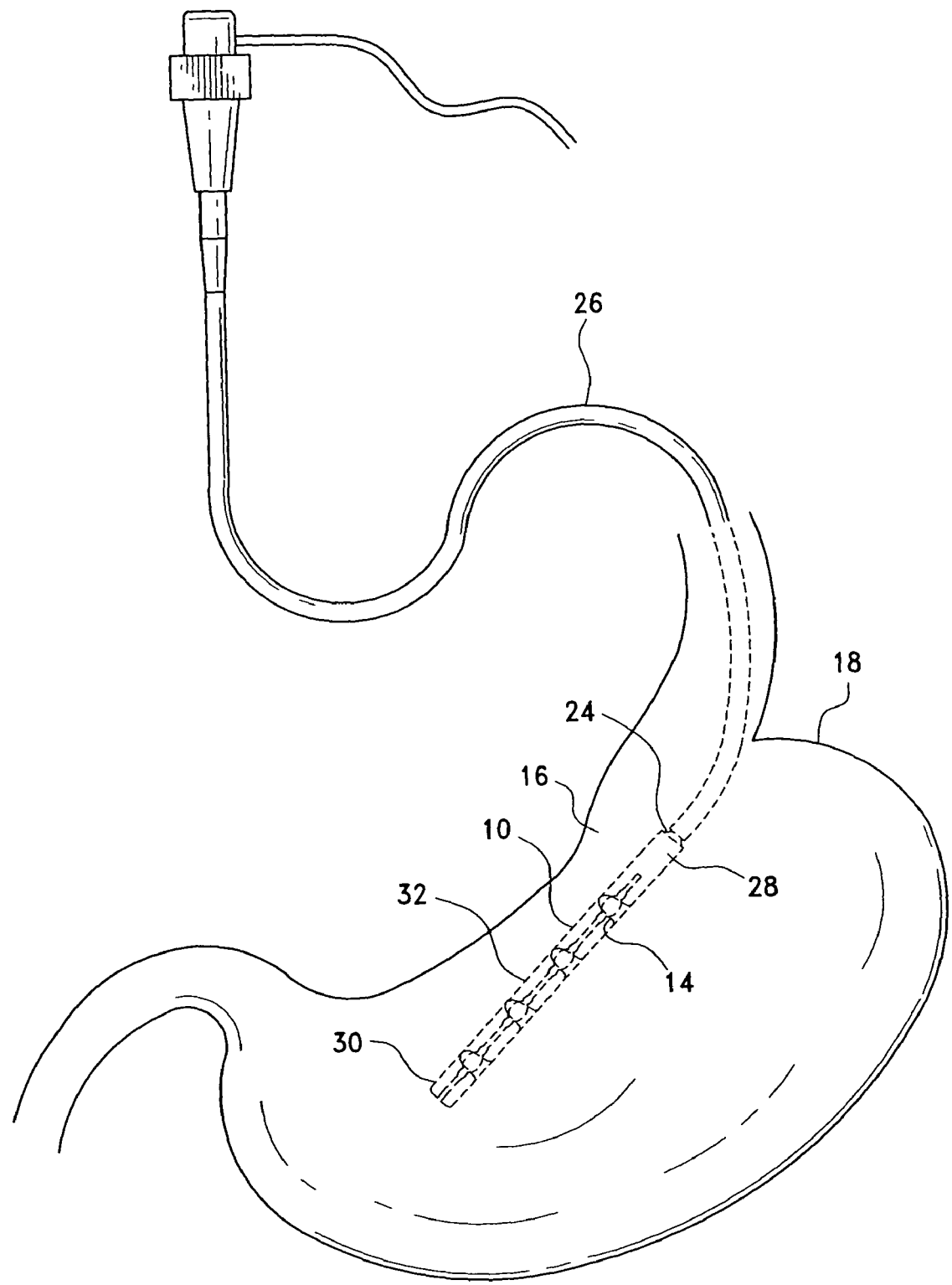
FIG. 1 is a perspective view of the present gastric reduction apparatus in use.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1, 2, 3, 4, 5, 6a and 6b, a first embodiment of an apparatus 10 and method for gastric reduction surgery is disclosed. In accordance with this invention, a gastric reduction apparatus 10 is provided which facilitates the secure attachment of purse string sutures 12a, 12b and a mattress stitch suture 14 to the gastric wall 16 allowing for the creation of a transoral passageway through the stomach 18. Although the present apparatus is described herein for use in performing gastric reduction surgery, those skilled in the art will appreciate the apparatus and the underlying concepts may be applied in various soft tissue apposition procedures where tissue is drawn together either permanently or temporarily.

Briefly, the anterior and posterior gastric walls 20, 22 are transorally joined in a linear fashion. The walls 20, 22 are secured at approximately 3 to 5 cm parallel to the lesser curvature starting substantially near the angle of Hiss and terminating at a length of approximately 10 to 12 cm. The present technique has proven to be an effective mechanism for weight reduction without the need for implementing more elaborate surgical techniques.

The gastric reduction apparatus 10 is shaped and dimensioned for selective attachment to the distal end 24 of a traditional endoscopic flexible gastroscope 26. The gastric reduction apparatus 10 is manipulated within the stomach 18 using conventional endoscopic manipulation techniques so as to position the gastric reduction apparatus 10 at a desired orientation within the stomach 18.

The gastric reduction apparatus 10 includes a proximal end 28 and a distal end 30. The proximal end 28 is shaped and dimensioned for secure attachment to the distal end 24 of the gastroscope 26 while the distal end 30 of the gastric reduction apparatus 10 is free for positioning within the stomach 18. Although a preferred embodiment employs an apparatus secured at the distal end of a gastroscope, those skilled in the art will certainly appreciate that the apparatus may be formed with its own shaft.

The gastric reduction apparatus 10 includes an elongated body 32. The body 32 is generally sinusoidal shaped with opposed anterior and posterior tissue engaging surfaces 34, 36 positioned along the top and bottom of the sinusoidal body 32. As will be explained below in greater detail, the tissue engaging surfaces 34, 36 are oriented such that a needle 38, 40 may substantially pass through either the entire anterior or posterior walls 20, 22 in a single pass. As to the amplitude of the sinusoidal body, the amplitude of the waves will vary for optimal use with each patient.

The extent of the sinusoidal waves are sufficient to draw opposed anterior and posterior walls 20, 22 of the stomach 18 into an overlapping configuration such that a needle 38, 40 may be respectively passed through the posterior or anterior wall 20, 22 for the purpose of placement of purse string sutures 12a, 12b in a manner discussed below in greater detail. While a specific sinusoidal waveform is disclosed in accordance with a preferred embodiment of the present invention, those skilled in the art will certainly appreciate that the extent of the sinusoidal waveform and the exact shape of the waveform may be varied without departing from the spirit of the present invention.

In accordance with a first embodiment, a double purse string attachment is employed. As such, the gastric reduction apparatus 10 only needs to offer a sinusoidal shape sufficient to place the respective anterior and posterior walls 20, 22 in an overlapping configuration such that a first needle 38 is passed through the anterior gastric wall 20 for placement of a first purse string suture 12a and subsequently a second needle 40 is passed through the posterior gastric wall 22 for placement of a second string suture 12b. Although the use of two needles is contemplated in accordance with a preferred embodiment of the present invention, those skilled in the art will appreciate that a single needle may be employed in the placement of both the first and second purse string sutures.

The gastric reduction apparatus 10 is composed of an elongated body 32 having a suction inlet 42. The apparatus 10 further includes a series of suction holes 44 along the respective anterior and posterior tissue engaging surfaces 34, 36. The suction holes 44 are in fluid communication with the suction inlet 42 and are shaped and dimensioned for drawing tissue therein upon the application of a vacuum within the gastric reduction apparatus 10. The suction holes 44 on opposite sides of the body 32 are oriented for simultaneously or sequentially drawing the anterior stomach wall 20 and the posterior stomach wall 22 into intimate contact with the anterior and posterior tissue engaging surfaces 34, 36 for the insertion of needles 38, 40 and the placement of sutures 12a, 12b in a manner discussed below in greater detail. Although an apparatus offering suction on opposed sides thereof is disclosed in accordance with a preferred embodiment of the present invention, those skilled in the art will appreciate that the apparatus may be constructed with a single suction side where it is desirable to apply the purse string sutures in a multiple step procedure.

The gastric reduction apparatus 10 also includes first and second needle passing channels 46, 48 respectively adjacent the anterior and posterior tissue engaging surfaces 34, 36. More specifically, the respective first and second needle passing channels 46, 48 generally pass through the center of the sinusoidal waveforms defined by the anterior and posterior tissue engaging surfaces 34, 36 such that the needles 38, 40 pass entirely through the tissue of the stomach wall 16 in a manner described below in greater detail. The gastric reduction apparatus 10 further includes suture passing channels 50 respectively aligned and associated with the first and second needle passing channels 46, 48. The suture passing channels 50 are shaped and dimensioned to permit the passage of the purse string sutures 12a, 12b therethrough during use of the present apparatus 10.

In practice, and in accordance with a first embodiment, the gastric reduction apparatus 10 uses suction, via the suction inlet 42 to draw the anterior and posterior gastric walls 20, 22 within the suction holes 44 and into intimate contact with the anterior and posterior tissue engaging surfaces 34, 36. The tissue is held in an undulated configuration in which the undulations are greater in depth than the thickness of tissue.

In this way, first and second long needles 38, 40 are respectively passed through the first and second needle passing channels 46, 48 and the undulated tissue in a manner fully passing through the anterior and posterior gastric walls 20, 22. It is contemplated a set of temporary barbs might be utilized to advance at an angle to the axis of the apparatus so as to add a measure of tissue holding during the present procedure.

Once the gastric reduction apparatus 10 is positioned within the stomach 18 and the vacuum is created for holding the tissue of the anterior and posterior stomach walls 20, 22 within the undulating anterior and posterior tissue engaging surfaces 34, 36 of the gastric reduction apparatus 10, the first and second long needles 38, 40 are respectively passed along the axis of the apparatus 10 through the needle passing channels 46, 48 located adjacent the opposed suction holes 44 and the anterior and posterior tissue engaging surfaces 34, 36. Referring to FIGS. 6a and 6b, at the head of each of the needles 38, 40, the suture 12a, 12b is fastened in place through the use of an anchor 51 secured at the distal end thereof. As those skilled in the art will appreciate, the anchor 51 is held within a distal recess 53 formed in the needle 38, 40 until the distal end of the needle 38, 40 reaches its desired location at which point the anchor 51 catches tissue upon extraction of the needle 38, 40 and the anchor 51 is released from the distal recess 53 for securing the suture at a desired location. As those skilled in the art will appreciate, although FIGS. 6a and 6b only show the first needle 38, the description applies equally to the second needle 40.

As each of the needles 38, 40 passes through the needle passing channels 46, 48 of the gastric reduction apparatus 10, the straight needles 38, 40 pierce the undulations in the stomach wall 16, passing alternately through mucosa, muscular layer, and serosa, and then back through the stomach wall 16 in a reverse direction resulting in a full thickness penetration.

Figure 2:
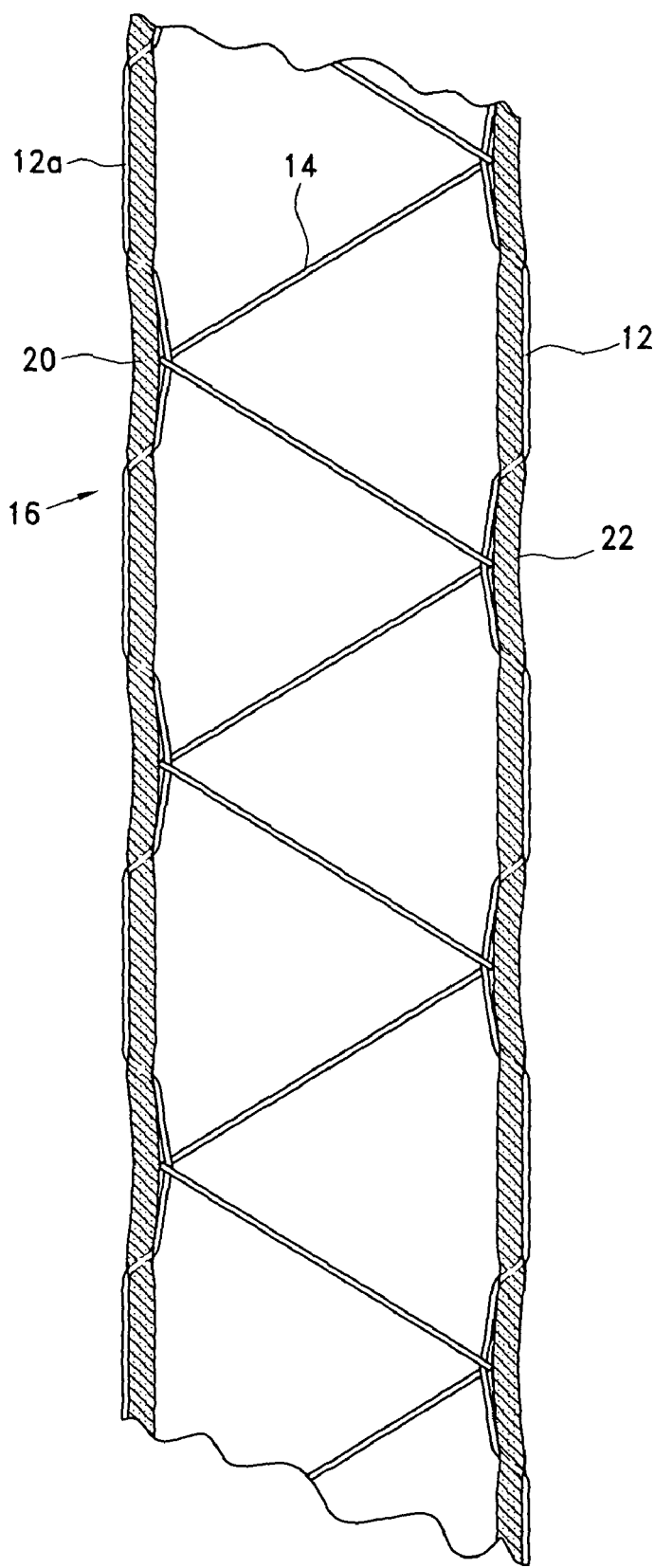
FIG. 2 is cross sectional view showing the suturing in accordance with the present invention.

The tight hold of the suction of the anterior and posterior stomach walls 20, 22 ensures that the respective first and second needles 38, 40 never touch adjacent organs. Once the suture 12a, 12b is drawn all the way through the tissue, the anchor 51 is released from within the distal recess 53 of the needle 38, 40 and the needle 38, 40 is retracted. With the needle 38, 40 removed, the anchor 51 and the purse string suture 12a, 12b are left behind as shown in FIGS. 2, 6a and 6b. The resulting purse string suture 12a, 12b is placed in both the posterior and anterior walls 20, 22 of the stomach in the manner described above.

Figure 3:
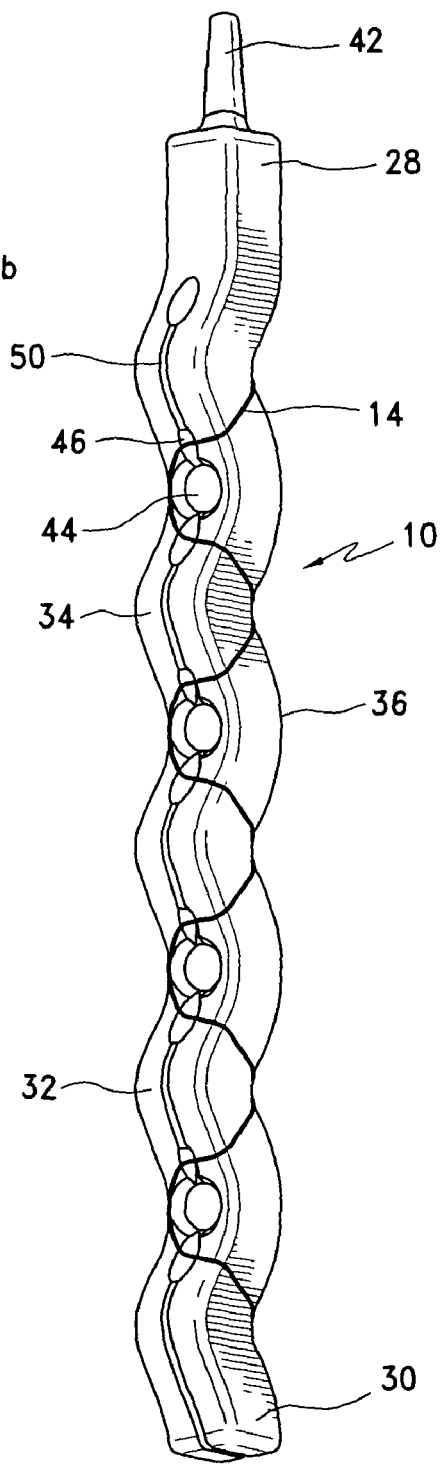
FIG. 3 is a perspective view of the gastric reduction apparatus.

Once a purse string suture 12a, 12b is properly positioned within both the anterior and posterior walls 20, 22 of the stomach 18, a pre-woven mattress stitch 14 preassembled on the gastric reduction apparatus 10 is released from the gastric reduction apparatus 10. The pre-woven mattress stitch suture 14 is secured to the purse sting sutures 12a, 12b such that drawing upon the mattress stitch suture 14 causes the anterior and posterior gastric walls 20, 22 to be drawn together in a manner creating a transoral cavity through the stomach (see FIG. 2). As shown in FIG. 3, the mattress stitch suture 14 is woven about the apparatus such that it alternately moves above and below the contemplated purse string suture line along both the anterior and posterior tissue engaging surface walls 34, 36. Although the use of a mattress stitch is disclosed in accordance with a preferred embodiment of the present invention, those skilled in the art will certainly appreciate that other stitch patterns may be used without departing from the spirit of the present invention.

Figure 9:
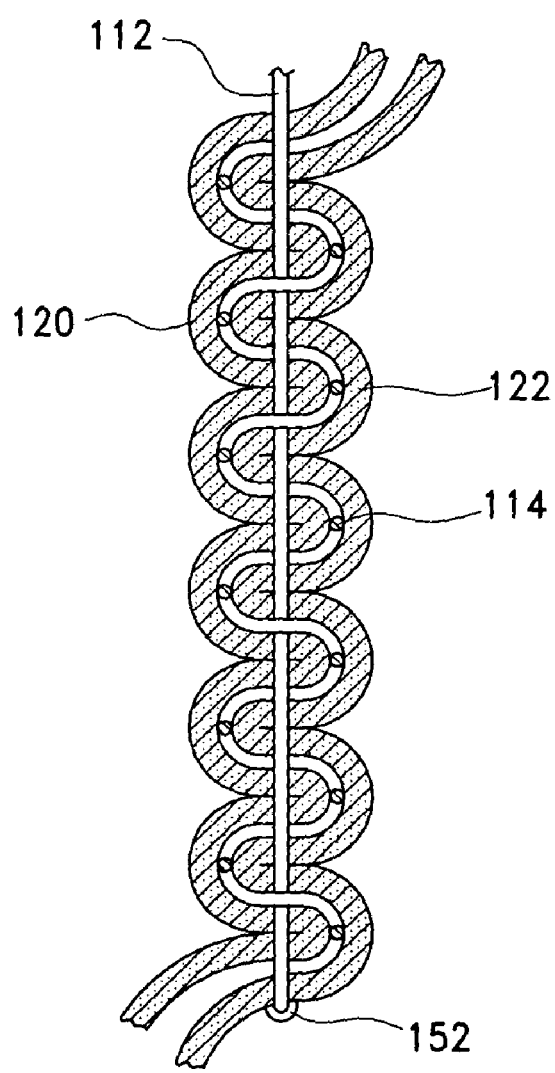
FIG. 9 is a cross sectional view showing suturing in accordance with the embodiment disclosed with reference to FIGS. 7 and 8.

With reference to FIGS. 7, 8 and 9, an alternate embodiment is disclosed wherein only a single needle passage is necessary for the application of the purse string suture 112 through the posterior and anterior walls 120, 122 of the stomach. More particularly, the body 132 of the gastric reduction apparatus 110 includes sinusoidal undulations that are very extreme such that the anterior and posterior walls 120, 122 of the stomach may be simultaneously drawn onto the gastric reduction apparatus 110 in an overlapping configuration. While a specific sinusoidal waveform is shown in accordance with a preferred embodiment of the present invention, those skilled in the art will certainly appreciate that the extent of the sinusoidal waveform and the exact shape of the waveform may be varied without departing from the spirit of the present invention.

Thereafter, a straight needle 138 is pushed through the needle passing channel 146 of the gastric reduction apparatus 110 such that it pierces the posterior and anterior walls 120, 122 in an alternating sequence. When the apparatus 110 is extracted, the purse string suture 112 remains and is secured to both the anterior and posterior walls 120, 122 of the stomach 118. The pre-woven mattress stitch 114 is similarly retained and pre-woven upon the gastric reduction apparatus 110 such that when the purse string suture 112 is cinched down a single suture approximates the anterior and posterior walls 120, 122 of the stomach 118. A suture clip 152 on a proximal end of the suture 112 will suffice in keeping the suture 112 in the cinched position maintaining the anterior and posterior walls 120, 122 in a joined relationship forming the transoral cavity.

Figure 10:
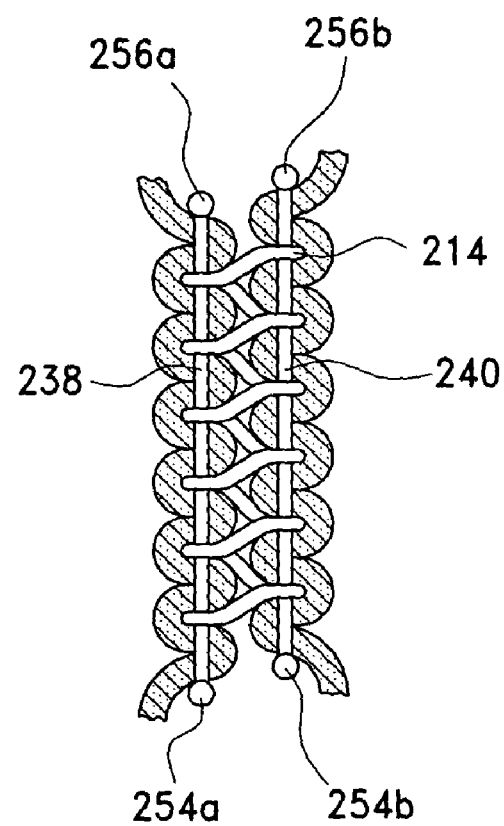
FIG. 10 is a cross sectional view showing suturing in accordance with yet another embodiment.

In accordance with yet a further embodiment, and with reference to FIG. 10, it is contemplated the needles 238, 240 passing through the undulations of the previously disclosed apparatus 10 may stay in place as opposed to applying a purse string suture to the anterior and posterior walls. In accordance with this embodiment, the ends of the needles 238, 240 will be terminated by attaching atraumatic balls 254a, 254b, 256a, 256b at both ends. The mattress stitch suture 214 will then be detachably connected to the apparatus 10. As with the previously described embodiments, the needle 238, 240, when passed down the apparatus 10, passes in and out of the pre-woven suture 214 while passing through the tissue. Thus, the pre-woven suture 214 is engaged with the straight needles 238, 240 on both sides of the apparatus 10. Upon extraction of the gastric reduction apparatus 10 from the body, the pre-woven mattress stitch 214 serves to approximate the two needles 238, 240 together.

Regardless of the embodiment employed in accordance with the present invention, various advantages are offered. In particular, the present invention offers a single shot device with no instrument exchange. In addition, the gastric pouch created in accordance with the present invention is highly standardized for repeatability. The suction drawing the stomach into the device also establishes the purse string without endangering the organs around the stomach and accomplishes this in a relatively quick procedure. Further, the present procedure requires only local anesthesia, minimal change to the body, it is reversible and revisable and may be performed in stages.

Inspection of the procedure may be achieved utilizing a distally mounted camera (CCD or CMOS) that plugs into the device to ensure the gastric wall has folded in a proper orientation. The camera may be mounted on an articulating or retroflexing arm to visualize backward with respect to the instrument. Alternatively, a two-camera unit may be employed for showing both the forward and rearward views of the stomach.

In addition, various knotting techniques may be employed in accordance with the present invention. For example, tissue cinching may be accomplished by throwing a sliding knot, tied outside the body, down the mouth and esophagus. Reinforcing materials may also be used to improve fixation, for example, mesh and buttressing may be employed within the spirit of the present invention.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A gastric reduction apparatus which facilitates the creation of a transoral linear passageway through the stomach, comprising:
   an elongated body including a proximal end and a distal end, the elongated body is generally sinusoidal shaped with at least one tissue engaging surface oriented such that a needle will pass therethrough, the elongated body includes a plurality of sinusoidal waveforms extending along an entire length of the elongate body between the proximal end of the elongated body and the distal end of the elongated body;
   the elongated body also includes at least one needle passing channel respectively formed adjacent the at least one tissue engaging surface, the at least one needle passing channel generally passes through the center of a sinusoidal waveform defined by the at least one tissue engaging surface such that a needle will pass entirely through stomach tissue contacting the tissue engaging surface of the elongated body;
   the elongated body further includes a suture passing channel.

2. The gastric reduction apparatus according to claim 1, wherein the elongated body is shaped and dimensioned for selective attachment to a distal end of an endoscopic flexible gastroscope.

3. The gastric reduction apparatus according to claim 1, wherein the elongated body includes opposed anterior and posterior tissue engaging surfaces positioned along the top and bottom of the elongated body.

4. The gastric reduction apparatus according to claim 3, wherein the elongated body includes first and second needle passing channels respectively formed adjacent the anterior and posterior tissue engaging surfaces.

5. The gastric reduction apparatus according to claim 4, wherein the respective first and second needle passing channels generally pass through the center of the sinusoidal waveform defined by the anterior and posterior tissue engaging surfaces such that a needle will pass entirely through stomach tissue contacting the anterior and posterior tissue engaging surfaces of the stomach wall.

6. The gastric reduction apparatus according to claim 3, wherein the elongated body includes a suction inlet and at least one suction holes along the respective anterior and posterior tissue engaging surfaces.

7. The gastric reduction apparatus according to claim 3, wherein the extent of the sinusoidal shape defining the anterior and posterior tissue engaging surfaces is to draw opposed anterior and posterior walls of the stomach into an overlapping configuration such that a needle may be respectively passed through the posterior or anterior walls for placement of purse string sutures.

8. The gastric reduction apparatus according to claim 1, wherein the elongated body is shaped and dimensioned for the creation of a purse string suture.

9. The gastric reduction apparatus according to claim 8, wherein the elongated body is shaped and dimensioned for the creation of a double purse string suture.

10. The gastric reduction apparatus according to claim 1, wherein the elongated body includes a suction inlet and a series of suction holes along the at least one tissue engaging surface.

11. The gastric reduction apparatus according to claim 1, wherein the elongated body includes sinusoidal undulations such that the anterior and posterior walls of the stomach are simultaneously drawn onto the gastric reduction apparatus in an overlapping configuration allowing a single needle to simultaneously pierce both the anterior and posterior walls of the stomach.

12. The gastric reduction apparatus according to claim 11, wherein the elongated body includes only a single needle passing channel.

13. The gastric reduction apparatus according to claim 1, wherein the needle includes a means of reducing trauma positioned at both ends thereof.

14. The gastric reduction apparatus according to claim 1, further including a pre-woven suture positioned about the elongated body.

15. A gastric reduction apparatus which facilitates the creation of a transoral linear passageway through the stomach, comprising:
   an elongated body including a proximal end and a distal end, the elongated body has a general waveform shape with opposed anterior and posterior tissue engaging surfaces positioned along opposite sides of the elongated body;
   the elongated body also includes first and second needle passing channels respectively formed adjacent the anterior and posterior tissue engaging surfaces, the first and second needle passing channels generally pass through the center of the waveform defined by the anterior and posterior tissue engaging surfaces such that a needle will pass entirely through stomach tissue contacting the tissue engaging surface of the elongated body;
   the elongated body further includes a suture passing channel;
   a first needle and a second needle shaped and dimensioned for respective passage through the first and second needle passing channels, each of the first needle and the second needle including a purse string suture secured thereto; and
   a mattress stitch suture secured about the elongated body for securing with the respective purse string sutures of the first needle and the second needle allowing for drawing anterior and posterior walls together upon actuation of the present gastric reduction apparatus.

16. The gastric reduction apparatus according to claim 15, wherein the elongated body includes a suction inlet and at least one suction holes along the respective anterior and posterior tissue engaging surfaces.

17. A gastric reduction apparatus which facilitates the creation of a transoral linear passageway through the stomach, comprising:
   an elongated body including a proximal end and a distal end, the elongated body has a general waveform shape with opposed anterior and posterior tissue engaging surfaces positioned along the opposite sides of the elongated body, the anterior tissue engaging surface being composed of a plurality of undulations and the posterior tissue engaging surface being composed of a plurality of undulations, the elongated body includes a plurality of waveforms extending along an entire length of an elongate body between the proximal end of the elongated body and the distal end of the elongated body;

the elongated body also includes first and second needle passing channels respectively formed adjacent the anterior and posterior tissue engaging surfaces, the first and second needle passing channels generally pass through the center of the waveform defined by the anterior and posterior tissue engaging surfaces such that a needle will pass entirely through stomach tissue contacting the tissue engaging surface of the elongated body; and the elongated body further includes a suture passing channel.

18. The gastric reduction apparatus according to claim 17, wherein the elongated body includes a suction inlet and at least one suction holes along the respective anterior and posterior tissue engaging surfaces.

19. A gastric reduction apparatus which facilitates the creation of a transoral linear passageway through the stomach, comprising:

an elongated body including a proximal end and a distal end, the elongated body has a general waveform shape with opposed anterior and posterior tissue engaging surfaces positioned along opposite sides of the elongated body;

the elongated body also includes first and second needle passing channels respectively formed adjacent the anterior and posterior tissue engaging surfaces, the first and second needle passing channels generally pass through the center of the waveform defined by the anterior and posterior tissue engaging surfaces such that a needle will pass entirely through stomach tissue contacting the tissue engaging surface of the elongated body;

the elongated body further includes a suture passing channel;

a first needle including a first suture secured thereto and a second needle including a second suture secured thereto, the first needle and the second needle being shaped and dimensioned for respective passage through the first and second needle passing channels; and a third suture secured about the elongated body for securing with the respective first and second sutures of the first needle and the second needle allowing for drawing anterior and posterior walls together upon actuation of the present gastric reduction apparatus.

20. The gastric reduction apparatus according to claim 19, wherein the first suture is a purse string suture.

21. The gastric reduction apparatus according to claim 19, wherein the second suture is a purse string suture.

22. The gastric reduction apparatus according to claim 19, wherein the third suture is a mattress stitch suture.

23. The gastric reduction apparatus according to claim 19, wherein the third suture is a mattress stitch suture.

* * * * *